(12) United States Patent
Ganshorn

(10) Patent No.: US 9,226,690 B2
(45) Date of Patent: Jan. 5, 2016

(54) METHOD FOR MEASURING DEAD LUNG SPACE

(76) Inventor: Peter Ganshorn, Münnerstadt (DE)

( * ) Notice: Subject to any disclaimer, the term of this patent is extended or adjusted under 35 U.S.C. 154(b) by 942 days.

(21) Appl. No.: 13/121,382

(22) PCT Filed: Sep. 10, 2009

(86) PCT No.: PCT/DE2009/001284
§ 371 (c)(1),
(2), (4) Date: Apr. 25, 2011

(87) PCT Pub. No.: WO2010/040332
PCT Pub. Date: Apr. 5, 2010

(65) Prior Publication Data
US 2011/0196252 A1    Aug. 11, 2011

(30) Foreign Application Priority Data
Oct. 7, 2008 (DE) .......................... 10 2008 050 497

(51) Int. Cl.
*A61B 5/08* (2006.01)
*A61B 5/091* (2006.01)
*A61B 5/087* (2006.01)

(52) U.S. Cl.
CPC *A61B 5/091* (2013.01); *A61B 5/087* (2013.01)

(58) Field of Classification Search
CPC ........... A61B 5/087; A61B 5/091; A61B 5/08
USPC ................................................... 600/529–538
See application file for complete search history.

(56) References Cited

U.S. PATENT DOCUMENTS

2001/0049478 A1* 12/2001 Starr ............................ 600/532
2007/0068528 A1*  3/2007 Bohm et al. ............. 128/204.23
2008/0289628 A1* 11/2008 Hallback et al. ......... 128/203.12

* cited by examiner

*Primary Examiner* — Patricia Mallari
*Assistant Examiner* — Eric Messersmith
(74) *Attorney, Agent, or Firm* — Edwin D. Schindler

(57) ABSTRACT

A method for determining anatomical dead space in a respiratory tract of a living organizm, include the steps of continuously and simultaneously measuring flow (F) and respiratory air density (D) during exhalation (EX) over time (T). The time is measured from the start of exhalation, in which the flow is greater than zero, until the dead space point at which, after significant decreases following the start, the respiratory air density merges to an approximately constant value. The integral of the flow is formed from the start point until the dead space end point, the measurements of the respiratory air density and the flow from the start until the dead space end point and during the short time, as that time span in which the respiratory air density assumes an approximately constant value, taken place multiple times in each case.

8 Claims, 2 Drawing Sheets

METHOD FOR MEASURING DEAD LUNG SPACE

BACKGROUND OF THE INVENTION

1. Technical Field of the Invention

Figure 1:
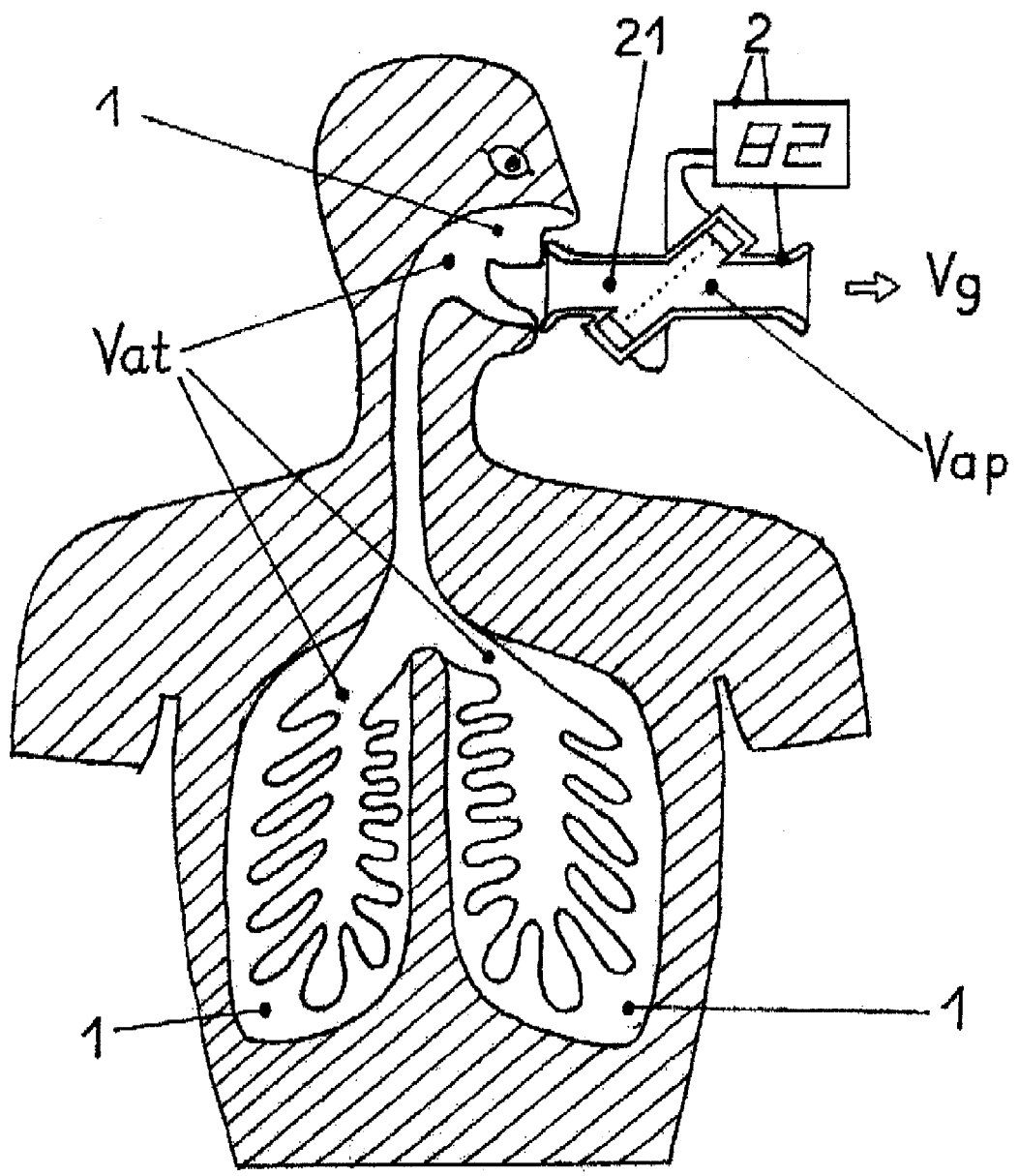

The invention relates to a method for determining the anatomical dead space in the respiratory tract of living organisms by the continuous and simultaneous measurement of flow (F) and respiratory air density (D) during exhalation (EX) over the time (T).

2. Description of the Prior Art

The respiratory tract includes the nose, pharynx, larynx, trachea, bronchia, bronchioli and alveoli. The trachea branches shortly before entering the lung into the left and right bronchi, also known as the bronchus principalis.

The lung is part of the respiratory tract and consists of air-carrying ducts, the bronchial system, which guides ambient air into the alveoli, in which gas is exchanged with the blood, that is to say oxygen is removed from the ambient air and carbon dioxide is added. The alveoli consist of very numerous and very small sacs, whose diameter is less than a millimeter. In an adult human, the internal surface area of all the alveoli is estimated at about 100 square meters.

The cavities of the respiratory tract, which guide the air from the mouth to the alveoli, are known as the "anatomical dead space", since they are not involved in gas exchange. Instead, they are only used for cleaning, preheating and moistening the respiratory air.

Since the lung unfortunately often has to battle with illnesses and/or can be pathologically changed, but a direct diagnosis of the lung itself is not possible, since it is not visible, imaging methods like X-ray equipment, magnetic resonance tomography (MRT) and ultrasound equipment are used to make fundamental statements about the change of the lungs. However, this method only permits qualitative diagnoses about changes of the lungs. Another problem is that the human respiration must not be interrupted during the diagnosis, and ideally should not be restricted at all.

The most diverse measuring instruments are therefore known in the prior art for quantitative determination of the lung function as a diagnosis aid for a multiplicity of lung diseases. Such instruments more or less accurately measure the flow of respiratory air, that is to say the air mass, and the respiratory air density during inhalation and exhalation.

Some known measurement instruments require the patient to exhale completely, inhale completely and/or not to breathe at all for a short time. Experience has shown that this breathing regime is not only experienced as unpleasant and inconvenient, but is also very often followed incorrectly, irregularly or with delay, as a consequence of which serious measurement errors can occur, which greatly restrict the diagnostic benefit of these devices.

Another disadvantage of many known methods is that the $CO_2$ concentration in the air is measured via complicated mass spectrometers or relatively slow IR analysers. This equipment is mostly very complex to manufacture and operate, and generally requires the cooperation of the patient. It can therefore not be used for small children, multimorbid and/or severely ill patients, and/or those with dementia. Another disadvantage is the very high costs and the large volume of the entire arrangement, including all ancillary equipment.

The common factor to all the devices is that they are not capable of distinguishing between the "dead space air" from the dead space of the lung system and the "alveolar air" from the air sacs—the alveoli—actively involved in gas exchange.

The anatomic dead space consists of the mouth and pharynx space, the contiguous airways, the trachea and, within the lung, of the bronchia, which extend from the windpipes into both lungs, and there continually branch until they reach the lung sacs.

According to the unanimous opinion of persons skilled in the art, the dead spaces do not take part in the gas exchange of the respiratory air into the blood at all, or only to a marginal extent. The function of the dead spaces is to clean, thermally condition (warm) the respiratory air and saturate the inhaled air to 100% relative humidity. Therefore, for precise determination of the air that has actually entered the alveoli, the alveolar air, the dead space volume of the entire respiratory volume can also be deducted.

In the prior art, the start of exhalation can be measured with good accuracy. However the transition from the dead space air expelled during exhalation to the alveolar air, i.e. the air volume coming back from the lung sacs, cannot be measured with the desirable accuracy. All the equipment and described principles of the prior art are too slow, too inaccurate, or both.

The German Offenlegungsschrift DE 1 918 566, Erich Jäger, of Apr. 11, 1989, describes a "device for examining lung function", in which, before the actual measurement, a "magnetic valve" opens, so that the "portion of the expiratory air corresponding to the dead space" flows out through the outlet. Therefore, very generally, a particular portion of the exhaled air is first classified as dead space air.

This device therefore refrains in advance from accurate measurement of the dead space volume, but is restricted to expelling a portion of the exhaled air unmeasured into the open that is so large that the measurement only takes place with alveolar air. However, this principle requires that only particular conditions and compositions in the air can be measured, but not the volume thereof.

A ratio between the dead space and alveolar space that is distorted for pathological reasons can therefore only be measured indirectly and hence only with very restricted accuracy with such an instrument.

German Offenlegungsschrift DE 28 12 379, Udo Smidt, discloses a device for lung diagnostics, in particular for diagnostic of lung emphysema, which values the greatly increased portion of the mixed air volume, compared to healthy persons, as an indicator. To this end, a gas analyser is preferably used, the $CO_2$ measurement sensor of which operates according to the infrared absorption principle. In addition, an inhalation stream receptor is necessary to determine the respiration volume. From the variation of $CO_2$ concentration with time and the respiration volume with time, the range of constant increase of $CO_2$ concentration after exhalation of the dead space air can be used for calculating the mixed air volume. The increase of the mixed air volume in ratio to the total volume is evaluated as an indicator of the severity of the lung emphysema.

The method could not become established at the time of its disclosure because of the, at that time, impracticably high effort for performing the computational functions, that is to say in the absence of the microprocessors that are available in the current state of the art. Another disadvantage is the complicated infrared absorption measurement sensor that was preferred at that time.

With modern microprocessor technology and better sensors, this method could be realized in the current state of the art. But, even then, there remains the disadvantage that the measurement of the actual, that is to say the functional, dead space volume is not possible, but can only be estimated indirectly with a very high tolerance.

In the absence of measurement methods, which are mostly too slow, it is hardly known that the transition from the dead space air to the alveolar air is marked by the dramatic decrease of the curve of respiratory air density over time to a value that is constant for a short time. That may be one reason why until now no measurement method has been known that permits this point to be determined with the desirable accuracy.

Figure 2:
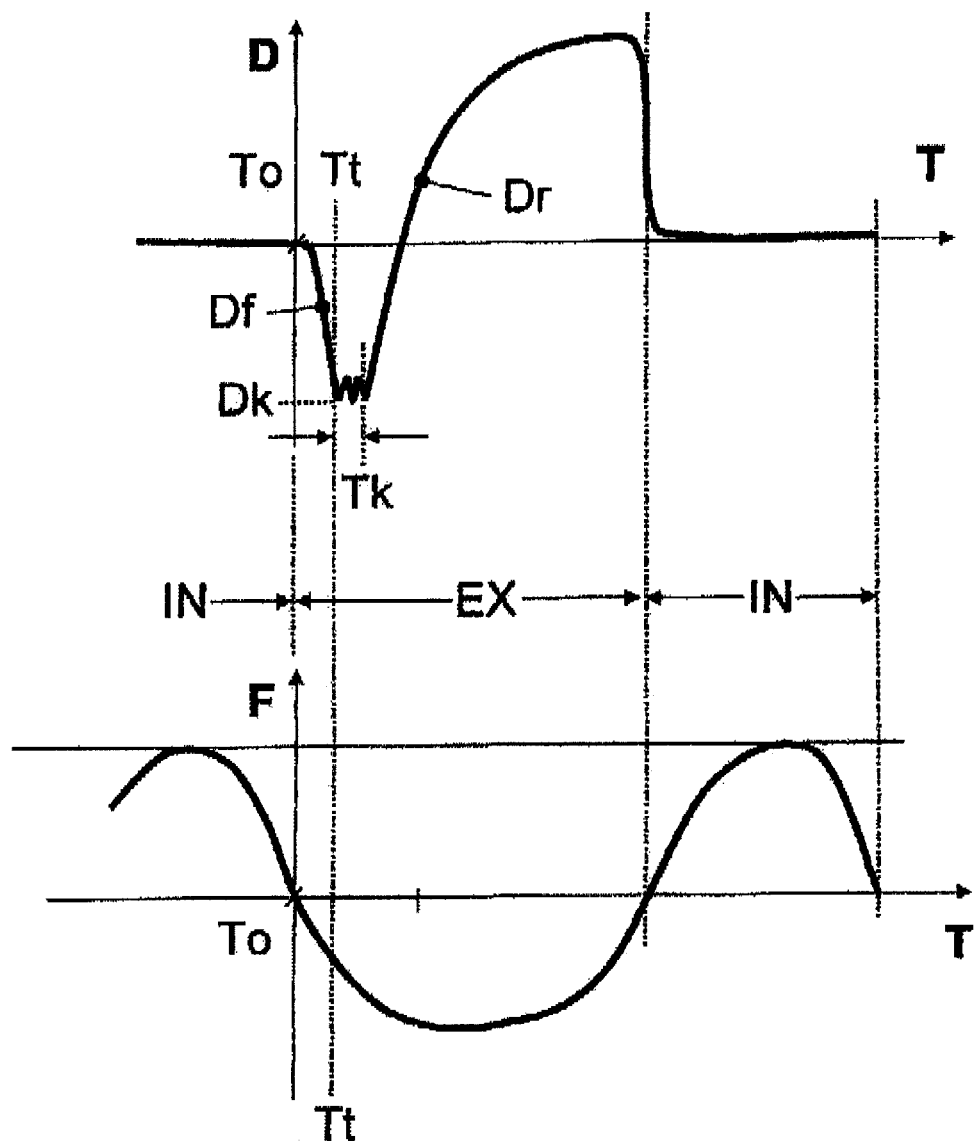

For example, the curve of $CO_2$ concentration with time, published in DE 28 12 379 under FIG. 2 does not show this decrease at all.

The portion of the expiration volume can be calculated using Bohr's dead space formula. With the following abbreviations Vat=Anatomic dead space volume
Vg=Breath volume
Di=$CO_2$ concentration of fresh air
De=$CO_2$ concentration of expirate
Da=$CO_2$ concentration of alveolar air The following sequences and relationships apply:

Before inspiration, the alveolar space and dead space are still filled with alveolar gas. After the Inspiration of the breath volume Vg, the alveolar space has expanded by Vat, but only the portion Vg-Vat reaches the alveolar space, while the rest remains in the dead space. The portion in the alveolar space mixes with the alveolar gas, so that the latter is refreshed. On expiration, first fresh air is exhaled from the dead space, then alveolar gas; the gas concentration then again reaches the same value as before inspiration. For the relationship between the individual parameters, the Bohr's formula applies:

$$Vat \cdot Di + (Vg - Vat) \cdot Da = Vg \cdot De$$

$$Vat = Vg \cdot \frac{Da - De}{Da}$$

A diagnosis according to this principle first requires the correct assignment to the areas of fresh air (Di), expirate (De) and alveolar air (Da) and, within this area, correct measurement of the $CO_2$ concentration in each case. According to Bohr's formula, the dead space can then be calculated. The result, however, is only accurate enough to maintain the proportionality of the respective $CO_2$ concentrations, which, however, can be changed by other effects, in particular in the case of a diseased lung. Based on Bohr's formula, therefore, only a trend, not an accurate diagnosis is possible.

SUMMARY OF THE INVENTION

Against this background, the invention has set itself the object of developing a method for more accurate measurement of the anatomical dead space volume, via the accurate measurement of the exchange of the escaping dead space air to the alveolar air.

The invention presents the solution that the time from the start of exhalation, in which the flow is greater than zero, until the dead space point, at which, after the significant decreases following the start, the respiratory air density changes to an approximately constant value, and the integral of the flow, is formed from the start until the dead space end point, the measurements of the respiratory air density and the flow from the start until the dead space end point and during the short time, as that time span in which the respiratory air density assumes an approximately constant value, taking place multiple times in each case.

The integral of the flow from the start of exhalation until the dead space end point corresponding, with higher accuracy than with all methods of the prior art, to the anatomical dead space volume of the respiratory tract in which no gas exchange takes place between the respiratory air and the blood. The term "dead space end point" describes the point in time at which all the respiratory air in the anatomical dead space has left the latter.

The time is characterized by the fact that the respiratory air density, after the start of exhalation and the subsequent decrease, changes to an approximately constant value. The accuracy with which this time is determined also determines the accuracy of the determination of the anatomical dead space, and is thereby a characterizing feature of the invention.

The biggest challenge in this is the relatively rapid decrease, since the decrease of the respiratory air density, for example for an adult human, extends over a period of only about 100 milliseconds, and then fluctuates about a constant value for a further 100 milliseconds.

It is readily apparent that a precise measurement of this curve profile requires multiple measurement points. The invention therefore proposes that the respiratory air density and the flow from the start of exhalation until the dead space end point should be measured at least 100 times. The measurement should preferably be made at least 500 times.

Since the approximately constant value then achieved also fluctuates, multiple measurements must also be made during this time. It is proposed that the respiratory air density and the flow in this time of an approximately constant value are measured approximately 30 times, preferably, however, at least 150 times.

To evaluate the curve profile, in one embodiment, an average should be formed in a higher-level control from the two ranges of the decrease and an approximately constant value, so that, as a result, two crossing straight lines on the time axis mark the dead space end point with relatively high accuracy.

The invention proposes as method for determining these two straight lines that the profile of the respiratory air density is saved in a memory. From the saved values, the dead space end point can then be determined very accurately with the following three steps: In the first step, the lowest value and a preselectable number of the next low values are selected from the profile of the respiratory air density, and in the time range extending therefrom, the average value is formed from all measurements and evaluated as a constant value.

In the second step, from the range from the start of exhalation until the constant value is first reached, a mid-point of the curve is selected with a preselectable width and, from all measurement values of this range, a straight line is determined with a particular gradient.

In the third step, the crossing point of these straight lines with the determined value for the constant value is evaluated as a time point for the dead space end point.

For performing such computational operations, in the prior art, microprocessors and the appropriate software are known, which operate at a fully adequate speed and adequate resolution.

Since, in the measurement, the measurement space volume of the measurement zone is additionally acquired, this volume must be subtracted from the measurement result. Since the internal volume of the measurement zone is known very accurately and since the flow within the measurement zone also runs approximately laminar, the measurement zone volume can be directly subtracted from the measurement result.

If, for example, the measurement sensors are disposed in the centre of the measurement zone, the anatomical dead space turns out to be the total of the measured volume from the start of exhalation until the dead space end point reduced by half of the measurement space volume.

or as a formula $$Vat = \sum_{T0}^{Tt} Vg - 1/2 Vap$$

where
Vat is the anatomical dead space volume,
Vg is the respiration volume measured in the measurement zone,
Vap is the measurement space volume of the measurement zone,
$T_0$ is the start of exhalation, and
Tt is the dead space end point, which marks the time from the start $T_0$ of exhalation until complete expulsion of the air inhaled into the anatomical dead space ($V_{et}$).

DETAILED DESCRIPTION OF THE PREFERRED EMBODIMENTS

The method according to the invention for lung dead space measurement can be used for any lung diagnosis device that has a measurement path for measuring the flow and the respiratory air density of the respiratory air as a function of time, and is equipped with a memory for storing the measurement values and a computer, for example a microprocessor, for supporting the measurement and for evaluating the stored measurements. This device must also have a display or at least an output unit for the measurement results.

A characterizing feature of the invention is that all measurements are repeated so rapidly that the values are registered with sufficient accuracy. A general rule of thumb is a repetition frequency of at least 1 kilohertz. At lower frequencies corresponding reductions in accuracy must be made.

A very interesting embodiment of the measurement zone is an ultrasound measurement zone, which is inclined at an angle to the respiration direction. With this measurement zone, the travel time of an ultrasound pulse directed inclined to the respiration stream during a breath can be measured very frequently, so that, in an evaluation unit, the current values of flow (air mass) and the respiratory air density can be calculated. These values are the basis for performing the method according to the invention.

A lung diagnosis device in which the method according to the invention is implemented can be equipped with additional diagnostic functions. It is, for example, conceivable to compare the determined ratio between alveolar air and dead space volume with a normal value, and to generate a ratio as result.

This ratio can be displayed directly on the device, e.g. with digits, by means of an analogue display and/or by means of a quasi-analogue display. Another variant is three, in each case single-stage display elements, such as, e.g., light emitting diodes, which are either illuminated or dark. A display sequence that is very simple and can therefore also be interpreted by the patient himself is a green light-emitting diode, if the ratio is in the normal range; a yellow light-emitting diode if the ratio deviates somewhat from the normal value, and a red light-emitting diode if the ratio deviates from the normal range to a critical extent.

All lung diagnosis devices operating with an ultrasound measurement zone according to the method of the invention have the advantage that they can dispense with a precise determination of the absolute value of respiratory air density and instead only need to register a ratio of the $CO_2$ densities, for which purpose a very high, reproducible accuracy can be achieved.

Compared to the prior art, the elaborate mass spectrometer can thereby be dispensed with and it becomes possible to produce a very small and compact unit, which can even be embodied as a handheld compact unit.

Another disadvantage is that breathing commands no longer need to be issued, for which reason such a unit is also suitable for the lung diagnosis of children, infants and babies, such as for assessing the normal growth of the lung.

Another important application is veterinary medicine, in which any type of breathing command is out of the question, and even applying the measurement zone in front of the respiratory tract of the animal is a challenge. In this case, the method according to the invention permits the first ever lung diagnostics for a multiplicity of different animals and their various lung diseases.

The method according to the invention thus greatly simplifies the qualitative and quantitative diagnosis of lung emphysema. This clinical syndrome characterises the irreversible overinflation of the ventilated spaces of the terminal bronchioles, that is to day the smallest air-filled lung structures at the end of the dead space of the lung before transition to the alveolar space, that is to say before the transition to the gas-exchanging air sacs.

Due to the loss of elasticity of the lung tissue, the contained air can no longer escape completely, as a result of which the pressure on the alveoli is increased, causing them to collapse and thereby trapping air spaces in the alveolar area, which can no longer expelled by exhalation. As a result, in the extreme case, still-functioning lung sacs become large non-functioning "emphysema sacs".

According to the method of the invention for lung dead space measurement, this clinical syndrome can not only be assessed as having occurred at all, but additionally also quantified, that is to say assigned to a particular severity of disease.

BRIEF DESCRIPTION OF THE DRAWING FIGURES

Further details and features of the invention are described below with reference to an example. This is not intended to restrict the invention, but only to explain it. In schematic view, FIG. 1 shows a symbolic section through a human torso with lung diagnosis device FIG. 2 shows schematic profiles of respiratory air density and flow

DETAILED DESCRIPTION OF THE DRAWING FIGURE

In detail, the figures show:

FIG. 1 shows, greatly simplified and stylized, the cross-section through a human torso, in which the respiratory tract (1) is drawn symbolically. The part of the respiratory tract from the mouth space to the bronchia is the anatomic dead space volume (Vat). Following this, within the lung, the bronchia are surrounded by the alveolae, which in FIG. 1 are not drawn individually but are represented by the area between symbolically sketched bronchia in the interior and the outline of the lung. It is thereby clear in FIG. 1 that the entire air guidance space in the human body is subdivided into the dead space (Vat) and the alveolar space.

FIG. 1 shows how a lung diagnosis apparatus (2) is applied to the patient's mouth. It includes a measurement zone (21), which extends from the mouthpiece to the opening for exhalation. In the centre thereof, two ultrasonic transmitters and receivers are arranged such that the sound runs at an angle to the breathing direction, which is symbolized by a dotted line.

In this manner, the travel time of the ultrasound and its influence by the respiratory air can be measured. In an evaluation unit—not shown here—the measurement values are saved and evaluation and—for example as shown in FIG. 1—can then be output by means of a simple seven-segment display on the upper portion of the lung diagnosis device (2).

In FIG. 1, the entire volume (Vg) measured in the measurement zone is represented by a double arrow before the measurement zone 21. It is very clear that the entire measured volume (Vg) is the total of the anatomical dead-space volume (Vat) and the alveolar volume—which is not shown in detail here—and the half measurement space volume (Vap) of the measurement zone.

In FIG. 1, it is clear that the ultrasound zone crosses the measurement zone 21 in its centre. Therefore, half—drawn in FIG. 1, left—of the measurement zone is also included in the measurement.

In FIG. 1, it also very quickly becomes clear that, to use the apparatus, the patient can breathe virtually unrestricted through the measurement zone 21, which is tubular in this case.

In FIG. 2, the upper curve of the schematic profile of the breathing air density (D) is drawn over a cycle consisting of exhalation (EX) and inhalation (IN). In the lower portion, on the same time axis, the profile of flow (F) is plotted.

In the upper curve, the respiratory air density (D), it can be clearly seen that, with the start of exhalation (EX), the respiratory air density (D) drops off steeply with the falling flank (Df) until it reaches the constant value (Dk). For the short time (Tk), the respiratory air density (D) fluctuates approximately about the constant value (Dk) and than merges into the rising flank (Dr). With the end of exhalation (EX) and the start of inhalation (IN), the respiratory air density (D) falls suddenly to zero again.

In the upper curve of FIG. 2, it can be clearly seen that the falling flank (Df) can be approximated by a straight line with limited computational outlay.

Likewise, FIG. 2 shows that the fluctuations about the constant value (Dk) can be combined with high precision by means of a single average value (Dk). If this average value (Dk) is plotted as a straight line—parallel to the time axis—it quickly becomes plausible in FIG. 2 that the intersection of these straight lines, with the failing flank (Df) of the variation of the respiratory air density, which has also been replaced by a straight line, reproduces the dead-space end point (Tt) with relatively high accuracy.

The lower curve, the flow (F), over time (T), makes it clear that, together with the—known—volume of the measurement zone (21), the dead-space volume (Vat) can be exactly calculated.

LIST OF REFERENCE CHARACTERS

1 Lung system
2 Lung diagnosis apparatus
21 Measurement zone of the lung diagnosis apparatus (2)
D Respiratory air density during exhalation (EX)
Df Falling respiratory air density after the start of exhalation (EX)
Dk Constant value of respiratory air density
Dr Rising flank of the variation of the respiratory air density
EX Exhalation
F Flow, velocity of the respiratory air during inhalation (IN) and exhalation (EX)
IN Inhalation
T Time
T0 Start of exhalation (EX)
Tk Short time during which the respiratory air density remains approximately at the value Dk
Tt Dead-space end point from the start $T_0$ of exhalation until the complete expulsion of the air inhaled into the anatomical dead space (Vat)
Vap Measurement space volume of the measurement zone 21
Vat Anatomical dead space volume
Vg Volume measured in the measurement zone 21

The invention claimed is:

1. A method for determining anatomical dead space (Vat) in a respiratory tract of a living organism, comprising the steps of:
   (a) continuously and simultaneously measuring flow (F) and respiratory air density (D) of respiratory air of a living organism during exhalation (EX) over time (T) via a lung diagnosis apparatus having an ultrasound measurement zone comprising at least one ultrasonic transmitter and receiver;
   (b) determining and storing, using an evaluation unit comprising a microprocessor that is operatively coupled to the lung diagnosis apparatus and that further comprises a memory, a start point (To) of exhalation (EX) at which the flow (F) becomes greater than zero and a dead space end point (Tt), at which the respiratory air density (D) becomes an approximately constant value (Dk) after significant decreases (Df) following the start point (To);
   (c) calculating and storing, using the evaluation unit, an integral of the flow (F) from the start point (To) of exhalation (EX) to the dead space end point (Tt); and,
   (d) repeating said steps (a), (b) and (c), as necessary, for completing a determination of the anatomical dead space (Vat) in the respiratory tract of a living organism.

2. The method for determining anatomical dead space (Vat) in a respiratory tract of a living organism according to claim 1, wherein said steps (a) and (b) are carried out at least 100 times.

3. The method for determining anatomical dead space (Vat) in a respiratory tract of a living organism according to claim 2, wherein said steps (a) and (b) are carried out at least 500 times.

4. The method for determining anatomical dead space (Vat) in a respiratory tract of a living organism according to claim 1, wherein the respiratory air density (D) and the flow (F) during the short time (Tk) are made at least approximately 30 times.

5. The method for determining anatomical dead space (Vat) in a respiratory tract of a living organism according to claim 4, wherein the respiratory air density (D) and the flow (F) during the short time (Tk) are made at least approximately 150 times.

6. The method for determining anatomical dead space (Vat) in a respiratory tract of a living organism according to claim 1, further comprising the steps of:
   saving a profile of the respiratory air density (D) from the respiratory air density fluctuations about the approximately constant value (Dk);
   selecting a lowest value and a preselectable number of next lowest values in a time range covered thereby, then averaging value of all measurement and evaluating as the approximately constant value (Dk);
   selecting, from a range from a start of exhalation until the approximately constant value (Dk) is reached for a first time, a central portion of a curve with a preselectable width;
   determining from all measurement values within the range, a straight line with a predetermined gradient; and, determining and evaluating an intersection of a plurality of straight lines with the value determined for the approximately constant value (Dk) as a time point for the dead space end point (Tt).

7. A lung diagnosis apparatus for determining anatomical dead space (Vat) in a respiratory tract of a living organism, comprising:

a measurement zone for measuring flow (F) and respiratory air density (D) of respiratory air over time (T) mountable on an air inlet of a respiratory tract of a living organism, said measurement zone including a measurement zone volume (Vap);

a measurement sensor mounted at a halfway point and within a symmetrical measurement volume;

a microprocessor operatively coupled to the measurement sensor and providing a memory for storing values measured in the measurement zone and calculated in the microprocessor;

the microprocessor configured to determine a start point (To) of exhalation (EX) at which the flow (F) becomes greater than zero until a dead space end point (Tt), at which the respiratory air density (D) becomes an approximately constant value (Dk) after significant decreases (Df) following the start point ($T_o$);

the microprocessor further configured to calculate and store an anatomical dead-space volume (Vat) being a total of measured volume (Vg) from a start point ($T_o$) of exhalation (EX) until a dead-space end point (Tt), reduced by half of said measurement zone volume (Vap) of said measurement zone in accordance with the formula:

$$V_{at} = \sum_0^t V_g - 1/2 V_{ap};$$

and an output unit for displaying results of the evaluations of the measurements stored in said memory.

8. The lung diagnosis apparatus for determining anatomical dead space (Vat) in a respiratory tract of a living organism according to claim 7, wherein said measurement zone is an ultrasound measurement zone inclined at an angle to a direction of breathing.

\* \* \* \* \*